(12) United States Patent
Wang et al.

(10) Patent No.: US 8,450,524 B2
(45) Date of Patent: May 28, 2013

(54) PROCESS FOR PRODUCING CARBOXYLIC ACID ANHYDRIDES

(75) Inventors: Hui Ting Wang, Fengshan (TW); Chia Jung Tsai, Kaohsiung (TW); Chia Hui Shen, Gangshan Township (TW)

(73) Assignee: China Petrochemical Development Corporation, Taipei (TW)

( * ) Notice: Subject to any disclaimer, the term of this patent is extended or adjusted under 35 U.S.C. 154(b) by 215 days.

(21) Appl. No.: 13/010,865

(22) Filed: Jan. 21, 2011

(65) Prior Publication Data

US 2012/0053366 A1 Mar. 1, 2012

(30) Foreign Application Priority Data

Aug. 31, 2010 (TW) ................................ 99129234 A

(51) Int. Cl.
*C07C 51/56* (2006.01)
(52) U.S. Cl.
USPC ......................................................... 562/891
(58) Field of Classification Search
CPC ..................................................... C07C 51/56
See application file for complete search history.

(56) References Cited

U.S. PATENT DOCUMENTS

| | | | |
|---|---|---|---|
| 3,560,539 A | 2/1971 | Booth | |
| 3,920,449 A | 11/1975 | Onoda et al. | |
| 3,978,148 A | 8/1976 | Citron | |
| 4,002,678 A | 1/1977 | Naglieri et al. | |
| 4,115,444 A | 9/1978 | Rizkalla | |
| 4,340,569 A | 7/1982 | Davidson et al. | |
| 4,340,570 A | 7/1982 | Davidson | |
| 4,341,741 A | 7/1982 | Davidson et al. | |
| 4,430,273 A | 2/1984 | Erpenbach et al. | |
| 5,298,586 A | 3/1994 | Beevor et al. | |
| 5,939,585 A * | 8/1999 | Ditzel et al. | ................... 562/519 |
| 7,553,991 B1 | 6/2009 | Chen et al. | |
| 2010/0145098 A1 | 6/2010 | Tu et al. | |

FOREIGN PATENT DOCUMENTS

| | | |
|---|---|---|
| CA | 1171879 | 7/1984 |
| CN | 1778468 A | 5/2006 |
| CN | 1876239 A | 12/2006 |
| EP | 0391680 | 10/1990 |
| TW | 097147075 | 6/2010 |

OTHER PUBLICATIONS

Shanghai Chemical Industry, 2006, vol. 31, Issue 07.
Shanghai Chemical Industry, 2006, vol. 31, Issue 07 (English Abstract).

* cited by examiner

*Primary Examiner* — Paul A Zucker
(74) *Attorney, Agent, or Firm* — Woodard, Emhardt, Moriarty, McNett & Henry LLP

(57) ABSTRACT

The present invention relates to a process for producing carboxylic acid anhydrides by the carbonylation reaction of a carboxylic acid ester, derived from an alcohol and a carboxylic acid, with carbon monoxide containing a small amount of hydrogen in a liquid reaction medium in the presence of a Group VIII B catalyst to produce a carboxylic acid anhydride. The liquid reaction medium comprises the Group VIII B catalyst, an organic halide, the carboxylic acid ester, an alkali metal salt, the carboxylic acid anhydride, the carboxylic acid, N-acetylimidazole as a protecting agent, and ethylidene diacetate (EDA) as an organic promoter. By making use of the protecting agent of N-acetylimidazole, metal ions in the reactor can be prevented from reacting with EDA so as to reduce the formation of hardly-soluble tars during the reaction. Also, the EDA organic promoter is kept at a certain content in the system to promote the overall carbonylation reaction rate.

17 Claims, 2 Drawing Sheets

PROCESS FOR PRODUCING CARBOXYLIC ACID ANHYDRIDES

FIELD OF THE INVENTION

The present invention relates to a process for producing carboxylic acid anhydrides by the carbonylation reaction of a derivative from an alcohol and a carboxylic acid with carbon monoxide, and in particular, a process for producing acetic anhydride by the carbonylation reaction of methyl acetate with carbon monoxide.

BACKGROUND TO THE INVENTION

Acetic anhydride, a well-known raw material widely used in the chemical industry, is mainly used to produce chemicals such as cellulose acetate and is an important raw material for synthesis of medicines, flavors, dyes, etc. There are currently three industrial processes for producing acetic anhydride, including the ketene process, the acetaldehyde oxidation process and the methyl acetate carbonylation process. Among these, the predominant is the ketene process, which is an old-fashioned and small-scale process and is adopted by many manufacturers; however, due to its high energy consuming and other drawbacks, the largest commercial scale production of acetic anhydride is currently the methyl acetate carbonylation process.

The ketene process is carried out by dissociating one water molecule or methane from the raw material of acetic acid or acetone at a high temperature to form ketene, which then reacts with acetic acid to form acetic anhydride. This process, which must be carried out at a reaction temperature of up to 750° C., will gradually go out of use in the future due to its high energy-consuming demand.

The acetaldehyde oxidation process makes use of the metal catalyst such as Mn, Co, Ni, Cu, etc. to oxidize acetaldehyde into peracetic acid, which further reacts with acetaldehyde to form acetic anhydride and a by-product of water. Acetic anhydride will further be hydrolyzed into acetic acid; that is, the final product will be the mixture of acetic anhydride and acetic acid. Therefore, the yield of acetic anhydride will be decreased.

The methyl acetate carbonylation process for producing acetic anhydride is an expanded application of the methanol carbonylation process for producing acetic acid and makes use of methyl acetate and carbon monoxide as the raw materials to produce acetic anhydride in the presence of transition metal catalysts (such as Rh, Ni, Co and Ir) and iodide promoter. The difference between the methyl acetate carbonylation process for producing acetic anhydride and the methanol carbonylation process for producing acetic acid is the water content of the reaction solution; the reaction solution of the former has to be kept in anhydrous conditions, while the reaction solution of the latter can have 1 to 20 wt. % of water content. Water has a great influence on the stability of the catalyst, and the high water content can facilitate the stability of the catalyst. Therefore, the stability of the catalyst in the anhydrous system of the methyl acetate carbonylation process is a primary problem that should be overcome. To solve the problem, a promoter or a co-catalyst such as alkali metal, phosphonium salt, ammonium salt and transition metal catalysts can be added to promote the stability and activity of the catalytic system. In addition, in the methyl acetate carbonylation process for producing acetic anhydride, a small amount of hydrogen must be added in the carbon monoxide feed gas to maintain the activity of the Rh catalyst.

Adding one or more promoters into the catalytic system to improve and promote the catalytic efficiency of the catalyst is the most important subject in these researches. U.S. Pat. No. 4,002,678 discloses that under an anhydrous condition, a carbonylation reaction is carried out by using nickel and chromium as the catalyst and carbon monoxide and methyl acetate or dimethyl ether as the raw materials in the presence of a halide and a trivalent organo-nitrogen compound or a trivalent organo-phosphorus compound. European Pub. No. 0391680 A1 discloses a process for preparing a carboxylic acid by using an alcohol or its ester under a water-containing condition, in which a quaternary ammonium iodide is used as a stabiliser of the rhodium catalyst. U.S. Pat. No. 4,115,444 discloses a process for preparing acetic anhydride, in which a Group VIIIB noble metal is used as the catalyst, together with multiple promoters comprising at least one metal of Groups IVB, VB, and VIB or a non-noble metal of Group VIIIB, or their compounds and a trivalent organo-nitrogen compound or a trivalent organo-phosphorus compound; the catalyst thereof is rhodium and iridium, the metal promoter is iron, cobalt, nickel, chromium, etc., and the organo-nitrogen compound promoter includes an amine, an imidazole, an imide, an amide, an oxime, etc. China Pub. Nos. 1876239 A and 1778468 A both disclose a catalytic system for synthesis of the carbonyl group of methyl acetate to an acid anhydride, in which a Rh compound is used as the catalyst and different amounts of alkyl iodides, hetero-polyacid salts and alkali metal iodine salts are used as the promoter; the performance of this catalytic system can be improved by the synergistic effect of the hetero-polyacid salts and the catalyst. U.S. Pat. No. 7,553,991 discloses that making use of different nitrogen-containing heterocyclic organic promoters in the carbonylation process to form with the Rh catalyst a stabilized complex can increase the carbonylation reaction rate, and adding such kind of organic promoter can lower the reaction temperature or keep the original reaction rate with a reduced LiI amount, which has the effect of saving energy and reducing production cost. Both U.S. Pat. Nos. 5,298,586 and 4,430,273 clearly disclose that in the Rh-catalyzed carbonylation process for producing carboxylic acid anhydride under anhydrous conditions, adding ionic iodides containing quaternary nitrogen can effectively improve the stability and solubility of the Rh catalyst. Taiwan Patent Application No. 097147075 discloses that adding an ionic liquid containing cations having a nitrogen-containing heterocyclic structure in the carbonylation process can increase the carbonylation reaction rate, and the ionic liquid is easily separated and recovered from the catalytic system due to its features such as thermal stability, chemical stability and low vapor pressure.

In the industrial methyl acetate carbonylation process for synthesizing acetic anhydride, a noble metal and iodide catalytic system is generally used. However, such a system usually produces hardly-soluble tars during the carbonylation process. Cao Yu, et al. of Shanghai Coking & Chemical Corp. had a research on the tar components in carbonylation synthesis for acetic anhydride and investigated the reaction mechanism of tar formation [Shanghai Chemical Industry, 2006, Vol. 31, Issue 07]. It was found that in a continuous carbonylation process, by-products such as acetaldehyde, vinyl acetate, ethylidene diacetate, etc. will be formed at the same time, and these by-products tend to react with the metal ions, especially noble metal ions, in the reactor and form hardly-soluble tars. Because the tar will reduce the activity of the catalyst and even encapsulate the iodides and noble metal catalyst to deactivate the catalyst and terminate the carbonylation reaction, lowering the carbonylation reaction rate, the control of tar formation is one of the key points for improving the carbonylation process.

As mentioned in many prior art patents, the formation of tar residues occurs in the carbonylation process of esters and ethers for producing acetic anhydride and ethylidene diacetate, and the tar residues tend to encapsulate the metal Rh and damage the Rh catalyst. Therefore, current patented technologies all focus on the method of removing the tar residues and recycling and reusing the Rh catalyst. The Rh recycling technologies can roughly classified into the extraction method, the precipitation method, the combustion method and the adsorption separation method. U.S. Pat. Nos. 4,340,569, 4,340,570 and 4,341,741 all disclose the noble metal, including rhodium, can be recycled by pretreatment with an alcohol, concentration via evaporation, treatment with an amine, and then extraction with hydrogen halide. Canada Pat. No. 1171879 discloses extraction of noble metals, including rhodium, with solvents which preferentially dissolve the tars; such solvents include alkanes, cycloalkanes, halogenated alkanes, and aromatic hydrocarbons, and particularly cyclohexane, toluene, and carbon tetrachloride. U.S. Pat. No. 3,920,449 discloses recycling the metal Rh by pyrolysis of the residues. U.S. Pat. No. 3,978,148 discloses recycling the metal Rh by adsorption of the metal Rh on the active carbon. U.S. Pat. No. 3,560,539 discloses making use of hydrogen and hydrides to reduce the formation of hydroxyl group from the carbonyl group in the tar, so as to release and thus recycle the Rh complex.

Therefore, it is still a main challenge in the future to develop a more economic process that can effectively prolong the life of Rh catalyst, reduce the tar formation, lower the complexity of the process and increase the space-time yield of carboxylic acid anhydrides at the same time.

SUMMARY OF THE INVENTION

The main object of the present invention is to provide a process for producing carboxylic acid anhydrides, which can keep a high reaction rate and reduce the tar formation under anhydrous conditions.

In order to achieve the aforementioned and other objects, the process for producing carboxylic acid anhydrides according to the present invention is carried out by the carbonylation reaction of a carboxylic acid ester, derived from an alcohol and a carboxylic acid, with carbon monoxide containing a small amount of hydrogen in a liquid reaction medium in the presence of a Group VIII B catalyst to produce a carboxylic acid anhydride.

The reaction medium mainly comprises a Group VIII B catalyst, an organic halide, a carboxylic acid ester, an alkali metal salt, ethylidene diacetate (EDA) as an organic promoter, N-acetylimidazole as a protecting agent, a carboxylic acid anhydride, a carboxylic acid, and a small amount of impurities. Specifically, in the liquid reaction medium, 300 to 3000 ppm of the Group VIII B catalyst, 5 to 30 wt. % of the organic halide, 1 to 15 wt. % of the alkali metal salt, 0.5 to 20 wt. % of EDA, 0.5 to 20 wt. % of N-acetylimidazole, and the carboxylic acid ester, the carboxylic acid anhydride, the carboxylic acid and the small amount of impurities are usually contained. The EDA organic promoter has to be kept at a certain content in the system, and its content can be kept by production from a side reaction of the system or by addition.

As used in the present invention, the alcohol is an aliphatic alcohol compound having 1 to 6 carbon atoms, the carboxylic acid is a carboxylic acid having 1 to 6 carbon atoms, and the CO gas taking part in the carbonylation reaction contains an appropriate amount of hydrogen to facilitate maintaining the catalytic activity. Preferably, the CO feed gas contains hydrogen at a concentration of from 0.1 to 10%. In addition, the Group VIII B catalyst is one or more catalysts selected from the group consisting of rhodium, nickel, cobalt and iridium; the organic halide can be a methyl halide such as, for example, methyl iodide; and the alkali metal salt can be a Group IA/IIA iodide salt such as, for example, lithium iodide, and the liquid reaction medium can contain 500 to 8000 ppm of Group IA/IIA metal ions to provide the corresponding content of iodine ions.

According to the present invention, the carbonylation reaction can be carried out at a temperature of from 160 to 240° C. and at a CO-controlled pressure of from 20 to 60 kg/cm$^2$.

In the Group VIIIB catalytic system for the carbonylation reaction of the present invention, the protecting agent of N-acetylimidazole is used to reduce the formation of hardly-soluble tars and the EDA organic promoter is used to increase the space-time yield of carboxylic acid anhydride, so that the operation range of the reaction can be expanded and the reaction can be carried out under milder conditions.

The process for producing carboxylic acid anhydrides according to the present invention will be described below in detail with reference to the following embodiments, and also as set forth in applicants' Taiwanese priority application No. 099129234, filed Aug. 31, 2010, the entire contents of which are hereby incorporated herein by reference. However, these embodiments are used mainly to assist in understanding the present invention, but not to restrict the scope of the present invention. Various possible modifications and alterations could be conceived of by one skilled in the art to the form and the content of any particular embodiment, without departing from the spirit and scope of the present invention, which is intended to be defined by the appended claims.

DESCRIPTION OF PREFERRED EMBODIMENTS

Figure 1:
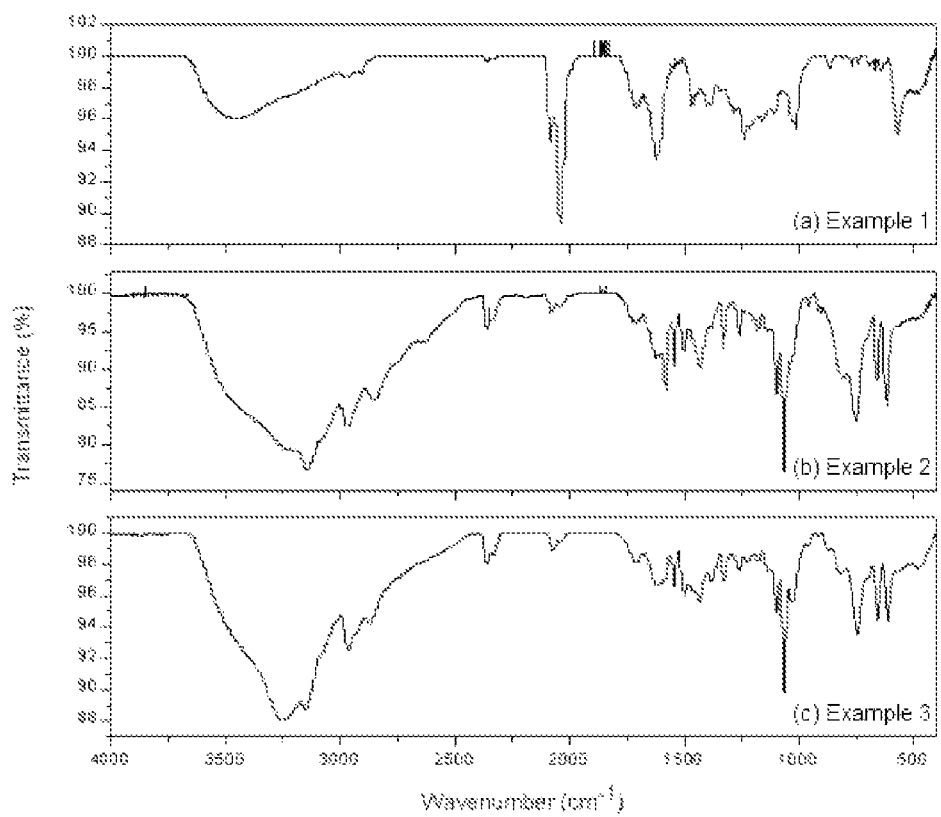
FIG. 1 shows the infrared spectra of Examples 1 to 3.

The features and effects of the present invention will be further explained with reference to the preferred embodiments below, which are, however, not intended to restrict the scope of the present invention.

The present invention can be operated as a batch process, in which the equipment as used mainly includes, for example, a one-liter reactor and a CO storage tank both made of anticorrosive materials. The reactor itself is provided with a speed-change motor capable of controlling the rotational speed, which can be appropriately adjusted so as to maintain a vapor/liquid well-mixing effect. The inside and the outside of the reactor are provided with a cooling coil and an electrically heating plate, respectively, so as to control and maintain a stable reaction temperature. A pressure control valve is provided between the reactor and the hydrogen and CO storage tanks so as to maintain and control the pressure of the main reactor.

One preferred embodiment of the present invention is to produce acetic anhydride by carrying out the carbonylation reaction of methyl acetate with carbon monoxide containing a small amount of hydrogen in the reactor. The reaction medium in the reactor for carrying out the carbonylation reaction is maintained to comprise a Group VIII B catalyst such as, for example, rhodium; a carboxylic ester derived from an alcohol and a carboxylic acid such as, for example, methyl acetate, or an ether derived from an alcohol compound such as, for example, dimethyl ether; an organic halide corresponding to the raw material of alcohol, such as, for example, methyl iodide; an alkali metal salt such as, for example, lithium iodide; a carboxylic acid anhydride such as, for example, acetic anhydride; a carboxylic acid such as, for example, acetic acid; the EDA organic promoter; and the protecting agent of N-acetylimidazole.

Alternatively, the present invention can be operated as a continuous process. Another preferred embodiment of the present invention is to continuously feed the raw material of methyl acetate, together with carbon monoxide containing a small amount of hydrogen, into the carbonylation reactor and react methyl acetate with carbon monoxide to produce acetic anhydride. The liquid reaction medium in the reactor comprises the Rh catalyst, methyl acetate, acetic acid, acetic anhydride, methyl iodide, an alkali metal salt, the EDA organic promoter, and the protecting agent of N-acetylimidazole. Corresponding to the continuously feeding reactor, the reaction product effluent comprises the product of acetic anhydride and the unreacted methyl acetate, acetic acid, methyl iodide, Rh catalyst, alkali metal salt, the EDA organic promoter, and the protecting agent of N-acetylimidazole. The liquid reaction product is continuously outputted to a flash tank (or an evaporator), the light constituents of the liquid reaction product are evaporated and discharged from the top of the flash tank to the purifying zone to further separate acetic acid and acetic anhydride, and the Rh catalyst and other heavy constituents at the bottom of the flash tank are reflowed to the reactor. After the product of acetic anhydride is separated in the purifying zone, acetic acid and other constituents (including methyl iodide, methyl acetate, etc.) are reflowed to the reactor. During the reaction process, methyl iodide, the alkali metal salt and the aforementioned organic promoter and protecting agent will not be consumed but are continuously circulated from the flash tank or the purifying zone to the reactor. If necessary, persons skilled in the art can consider adjusting the contents of the constituents of the reaction medium in accordance with the real operation situation.

The following Examples 1 to 6 are used to demonstrate that N-acetylimidazole can prevent metal ions, especially noble metal ions (for example, the Rh catalyst), from reacting with ethylidene diacetate and thus can reduce the formation of hardly-soluble tars during the reaction.

Example 1

After 0.29 g of ethylidene diacetate, 0.37 g of $IrCl_3 \cdot XH_2O$ (in which Ir atom accounts for 52.5%) and 100 ml of ethanol were added into a reaction flask and heated to 100° C., a reaction was carried out under reflux for 20 hours. The product, after cooled to normal temperature, was filtered to obtain black precipitated solids and a tawny solution. The tawny solution was concentrated, washed with ether, and then dried to remove the solvent. The infrared spectrum of the final product was determined ((a) in FIG. 1) and was taken as a control experiment.

Example 2

After 0.22 g of N-acetylimidazole, 0.37 g of $IrCl_3 \cdot XH_2O$ (in which Ir atom accounts for 52.5%) and 100 ml of ethanol were added into a reaction flask and heated to 100° C., a reaction was carried out under reflux for 20 hours. The product, after cooled to normal temperature, was filtered to obtain yellow solids and a yellow solution. The yellow solution was concentrated, washed with ether, and then dried to remove the solvent. The infrared spectrum of the final product was determined ((b) in FIG. 1) and was taken as a control experiment.

Example 3

After 0.29 g of ethylidene diacetate, 0.22 g of N-acetylimidazole, 0.37 g of $IrCl_3 \cdot XH_2O$ (in which Ir atom accounts for 52.5%) and 100 ml of ethanol were added into a reaction flask and heated to 100° C., a reaction was carried out under reflux for 20 hours. The product, after cooled to normal temperature, was filtered to obtain yellow solids and a yellow solution. The yellow solution was concentrated, washed with ether, and then dried to remove the solvent. The infrared spectrum of the final product was determined ((c) in FIG. 1).

By comparing the infrared spectrum of the Example 3 with those of the Examples 1 and 2, it is obvious that the spectrum signal of the Example 3 is similar to that of the Example 2; in other words, the coordination ability of N-acetylimidazole with Ir ions is better, which demonstrates that addition of such kind of protecting agent according to the present invention can indeed prevent ethylidene diacetate from reacting with Ir ions.

Example 4

Figure 2:
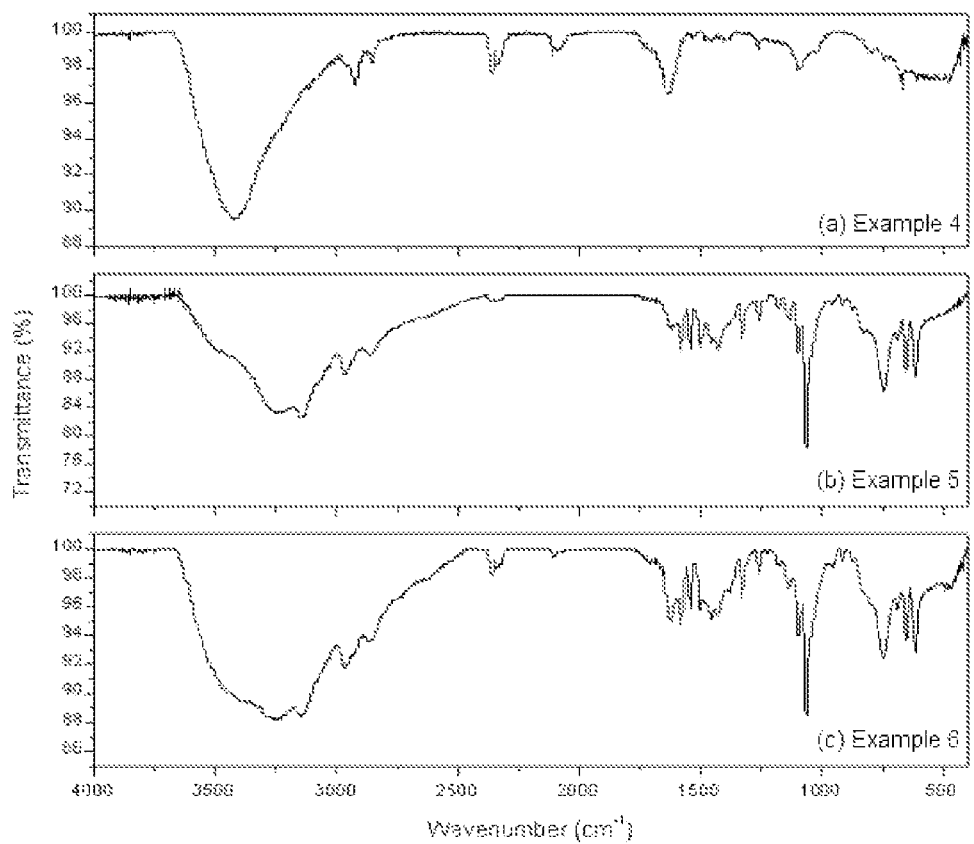
FIG. 2 shows the infrared spectra of Examples 4 to 6.

After 0.29 g of ethylidene diacetate, 0.27 g of $RhCl_3 \cdot XH_2O$ (in which Rh atom accounts for 38%) and 100 ml of ethanol were added into a reaction flask and heated to 100° C., a reaction was carried out under reflux for 20 hours. The product, after cooled to normal temperature, was filtered to obtain black precipitated solids and a light yellow solution. The light yellow solution was concentrated, washed with ether, and then dried to remove the solvent. The infrared spectrum of the final product was determined ((a) in FIG. 2) and was taken as a control experiment.

Example 5

After 0.22 g of N-acetylimidazole, 0.27 g of $RhCl_3 \cdot XH_2O$ (in which Rh atom accounts for 38%) and 100 ml of ethanol were added into a reaction flask and heated to 100° C., a reaction was carried out under reflux for 20 hours. The product, after cooled to normal temperature, was filtered to obtain a small amount of black precipitated solids and a red solution. The red solution was concentrated, washed with ether, and then dried to remove the solvent. The infrared spectrum of the final product was determined ((b) in FIG. 2) and was taken as a control experiment.

Example 6

After 0.29 g of ethylidene diacetate, 0.22 g of N-acetylimidazole, 0.27 g of $RhCl_3 \cdot XH_2O$ (in which Rh atom accounts for 38%) and 100 ml of ethanol were added into a reaction flask and heated to 100° C., a reaction was carried out under reflux for 20 hours. The product, after cooled to normal temperature, was filtered to obtain a small amount of black precipitated solids and a red solution. The red solution was concentrated, washed with ether, and then dried to remove the solvent. The infrared spectrum of the final product was determined ((c) in FIG. 2).

By comparing the infrared spectrum of the Example 6 with those of the Examples 4 and 5, it is obvious that the spectrum signal of the Example 6 is similar to that of the Example 5; in other words, the coordination ability of N-acetylimidazole with Rh ions is better, which demonstrates that addition of such kind of protecting agent according to the present invention can indeed prevent ethylidene diacetate from reacting with Rh ions.

The following Comparative Example 1 and Examples 7 to 15 are used to demonstrate that the EDA organic promoter present in the system at a certain amount will facilitate increasing the space-time yield of acetic anhydride.

Comparative Example 1

In this comparative example, a batch process without adding the organic promoter of the present invention was used, as a comparative experiment, to carry out the carbonylation reaction. The amount of each constituent fed into the reactor was: 43 wt. % of methyl acetate, 18 wt. % of methyl iodide, 18 wt. % of acetic anhydride, lithium iodide (4000 ppm of Li ion), 1400 ppm of the Rh catalyst, and an appropriately balanced amount of acetic acid as a solvent. The reactor into which the mixture of the aforementioned reactants had been fed was firstly pressurized with hydrogen to 1 kg/cm$^2$, and then carbon monoxide was introduced into the reactor, followed by a gradual elevation of temperature. After the set temperature for the reaction was reached, carbon monoxide was resupplied so that the inner pressure of the system reached 27 kg/cm$^2$. During the reaction, carbon monoxide kept on being resupplied with its consumption so that the pressure stably maintained 27 kg/cm$^2$. The amount of CO consumption was recorded and sampling was conducted for analysis to calculate the unit space-time yield (STY) of acetic anhydride (unit: mole/liter*hour).

Examples 7-9

Influence of Addition of Organic Promoter on Reaction Rate

The carbonylation reactions were carried out under the same conditions as the Comparative Example 1, except that 1 wt. %, 3 wt. % and 5 wt. % of the EDA organic promoter were added in the initial reaction media, respectively. The results of the Examples 7-9 and the Comparative Example 1 were recorded in Table 1 where the Comparative Example 1 was a blank experiment that no EDA organic promoter was added. It is obvious from Table 1 that the STY values of the carbonylation reaction with different amounts of the EDA organic promoter added were all increased by different levels and reached at least 7 gmol/L*h or above, which shows the addition of such kind of organic promoter according to the present invention can indeed increase the unit space-time yield of acetic anhydride.

TABLE 1

Influence of addition of organic promoter on reaction rate

| Reagent | Amount of EDA added (wt. %) | Temp. (° C.) | Pressure (Kg/cm$^2$) | LiI (Li ppm) | STY (gmol/L*hr) |
|---|---|---|---|---|---|
| CEx. 1 | — | — | 190 | 27 | 4000 | 6.40 |
| Ex. 7 | EDA | 1 | 190 | 27 | 4000 | 7.04 |
| Ex. 8 | | 3 | 190 | 27 | 4000 | 7.25 |
| Ex. 9 | | 5 | 190 | 27 | 4000 | 7.04 |

Examples 10-13

Influence of Reaction Temperature and Organic Promoter on Reaction Rate

The carbonylation reactions were carried out under the same conditions as the Comparative Example 1, except that 3 wt. % of the EDA organic promoter was added in the initial reaction media and the reaction temperature was changed. The results were recorded in Table 2. It is obvious from Table 2 that the STY values of the carbonylation reaction can still be increased by adding the organic promoter and changing the reaction temperature, which shows the addition of such kind of organic promoter under different reaction temperatures according to the present invention can indeed increase the yield of acetic anhydride. Also, from the comparison between the Examples 10 and 11 and the Comparative Example 1, adding such kind of organic promoter can have a better reaction rate at a lowered reaction temperature, which is energy-saving and can lower the production cost.

TABLE 2

Influence of reaction temperature and organic promoter on reaction rate

| Reagent | Amount of EDA added (wt. %) | Temp. (° C.) | Pressure (Kg/cm$^2$) | LiI (Li ppm) | STY (gmol/L*hr) |
|---|---|---|---|---|---|
| CEx. 1 | — | — | 190 | 27 | 4000 | 6.40 |
| Ex. 8 | EDA | 3 | 190 | 27 | 4000 | 7.25 |
| Ex. 10 | | 3 | 180 | 27 | 4000 | 6.85 |
| Ex. 11 | | 3 | 185 | 27 | 4000 | 7.02 |
| Ex. 12 | | 3 | 195 | 27 | 4000 | 7.25 |
| Ex. 13 | | 3 | 200 | 27 | 4000 | 7.48 |

Examples 14-15

Influence of Reaction Pressure and Organic Promoter on Reaction Rate

The carbonylation reactions were carried out under the same conditions as the Comparative Example 1, except that 3 wt. % of the EDA organic promoter was added in the initial reaction media and the reaction pressure was changed. The results were recorded in Table 3. It is obvious from Table 3 that the STY values of the carbonylation reaction can indeed be increased by adding the organic promoter and increasing the reaction pressure, which shows the addition of such kind of organic promoter under different reaction pressures according to the present invention can indeed increase the yield of acetic anhydride.

TABLE 3

Influence of reaction pressure and organic promoter on reaction rate

| Reagent | Amount of EDA added (wt. %) | Temp. (° C.) | Pressure (Kg/cm$^2$) | LiI (Li ppm) | STY (gmol/L*hr) |
|---|---|---|---|---|---|
| CEx. 1 | — | — | 190 | 27 | 4000 | 6.40 |
| Ex. 8 | EDA | 3 | 190 | 27 | 4000 | 7.25 |
| Ex. 14 | | 3 | 190 | 24 | 4000 | 7.24 |
| Ex. 15 | | 3 | 190 | 30 | 4000 | 7.48 |

What is claimed is:

1. A process for producing carboxylic acid anhydrides by the carbonylation reaction of a carboxylic acid ester, derived from an alcohol and a carboxylic acid, with carbon monoxide containing a small amount of hydrogen in a liquid reaction medium in the presence of a Group VIII B catalyst to produce a carboxylic acid anhydride, the reaction medium comprising the Group VIII B catalyst, an organic halide, the carboxylic acid ester, an alkali metal salt, the carboxylic acid anhydride, the carboxylic acid, N-acetylimidazole as a protecting agent, and ethylidene diacetate (EDA) as an organic promoter, wherein the content of the organic promoter in the reaction system is kept by producing the organic promoter from a side reaction or by further adding the organic promoter into the reaction system, wherein the content of the organic promoter of ethylidene diacetate is kept at 0.5 to 20 wt. %.

2. The process according to claim 1, wherein the alcohol is an alcohol having 1 to 6 carbon atoms.

3. The process according to claim 1, wherein the carboxylic acid is a carboxylic acid having 1 to 6 carbon atoms.

4. The process according to claim 1, wherein the carboxylic acid ester is methyl acetate.

5. The process according to claim 1, wherein the carboxylic acid is acetic acid.

6. The process according to claim 1, wherein the carboxylic acid anhydride is acetic anhydride.

7. The process according to claim 1, wherein the carbonylation reaction is carried out at a temperature of from 160 to 240° C.

8. The process according to claim 1, wherein the carbonylation reaction is carried out at a pressure of from 20 to 60 kg/cm².

9. The process according to claim 1, wherein the reaction medium contains the Group VIII B catalyst at a total concentration of from 300 to 3000 ppm.

10. The process according to claim 1, wherein the Group VIII B catalyst is one or more catalysts selected from the group consisting of rhodium, nickel, cobalt and iridium.

11. The process according to claim 1, wherein the organic halide is a methyl halide.

12. The process according to claim 11, wherein the methyl halide is methyl iodide.

13. The process according to claim 1, wherein the reaction medium contains 5 to 30 wt. % of organic halide.

14. The process according to claim 1, wherein the carbon monoxide feed gas contains hydrogen at a concentration of from 0.1 to 10%.

15. The process according to claim 1, wherein the alkali metal salt is a Group IA/IIA iodide salt.

16. The process according to claim 15, wherein the reaction medium contains 500 to 8000 ppm of Group IA/IIA metal ions to provide the corresponding content of iodine ions.

17. The process according to claim 1, wherein the protecting agent of N-acetylimidazole is added at a content of 0.5 to 20 wt. %.

* * * * *